US00PP34891P2

(12) United States Plant Patent
Spil

(10) Patent No.: US PP34,891 P2
(45) Date of Patent: Jan. 3, 2023

(54) ***ANEMONE* PLANT NAMED 'IFANFA'**

(50) Latin Name: *Anemone hupehensis*
Varietal Denomination: IFANFA

(71) Applicant: INNOFLORA PLANT BREEDING B.V., Heerhugowaard (NL)

(72) Inventor: Glenn Spil, Zuidermeer (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 17/877,910

(22) Filed: Jul. 30, 2022

(51) Int. Cl.
*A01H 5/02* (2018.01)
*A01H 6/72* (2018.01)

(52) U.S. Cl.
USPC ..... Plt./263.1
CPC ..... *A01H 6/72* (2018.05)

(58) Field of Classification Search
USPC ..... Plt./263.1
CPC ..... A01H 6/72; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Anemone* plant named 'IFANFA', characterized by its upright and uniform plant habit; moderately vigorous to vigorous growth habit; early and freely flowering habit; long flowering period; large single flowers that are reddish purple in color; and good garden performance.

2 Drawing Sheets

Figure 1:
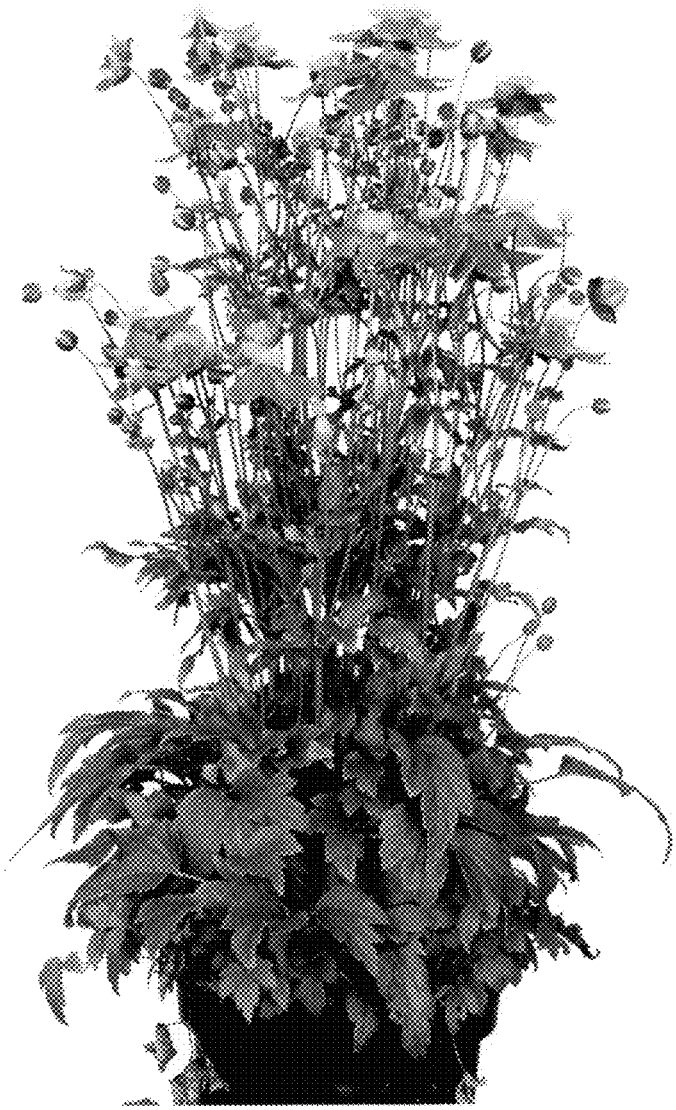

Botanical designation: *Anemone hupehensis*.
Cultivar denomination: 'IFANFA'.

STATEMENT REGARDING PRIOR DISCLOSURES BY APPLICANT

An European Plant Breeder's Rights application for the instant plant was filed by the Applicant on Nov. 26, 2021, application number 2021/3056. Foreign priority is not claimed to this application.

BACKGROUND OF THE INVENTION

The present invention relates to a new and distinct cultivar of *Anemone*, botanically known as *Anemone hupehensis* and hereinafter referred to by the name 'IFANFA'.

The new *Anemone* plant is a product of a planned breeding program conducted by the Inventor in Heerhugowaard, The Netherlands. The objective of the breeding program is to create new vigorous and fast-growing *Anemone* plants with numerous attractive flowers.

The new *Anemone* plant originated from a cross-pollination made by the Inventor in July, 2017 in a controlled greenhouse environment in Heerhugowaard, The Netherlands of a proprietary selection of *Anemone hupehensis* identified as code number 148-14-k020-11, not patented, as the female, or seed, parent with a proprietary selection of *Anemone hupehensis* identified as code number 148-12-k002-01, not patented, as the male, or pollen, parent. The new *Anemone* plant was discovered and selected by the Inventor as a single flowering plant within the progeny of the stated cross-pollination in a controlled greenhouse environment in Heerhugowaard, The Netherlands in August, 2018.

Asexual reproduction of the new *Anemone* by in vitro meristem culture in a controlled environment in Heerhugowaard, The Netherlands since August, 2018 has shown that the unique features of this new *Anemone* plant are stable and reproduced true to type in successive generations.

SUMMARY OF THE INVENTION

Plants of the new *Anemone* have not been observed under all possible combinations of environmental conditions and various cultural practices. The phenotype may vary somewhat with variations in environmental conditions such as temperature and light intensity without, however, any variance in genotype.

The following traits have been repeatedly observed and are determined to be the unique characteristics of 'IFANFA'. These characteristics in combination distinguish 'IFANFA' as a new and distinct *Anemone* plant:

1. Upright and uniform plant habit.
2. Moderately vigorous to vigorous growth habit.
3. Early and freely flowering habit.
4. Long flowering period.
5. Large single flowers that are reddish purple in color.
6. Good garden performance.

Plants of the new *Anemone* can be compared to plants of the female parent selection. Plants of the new *Anemone* differ primarily from plants of the female parent selection in the following characteristics:

1. Plants of the new *Anemone* have single-type flowers whereas plants of the female parent selection have double-type flowers.
2. Flowers of plants of the new *Anemone* have reddish purple-colored sepals whereas flowers of plants of the female parent selection have pink-colored sepals.

Plants of the new *Anemone* can be compared to plants of the male parent selection. Plants of the new *Anemone* differ primarily from plants of the male parent selection in the following characteristics:

1. Plants of the new *Anemone* have single-type flowers whereas plants of the male parent selection have double-type flowers.
2. Flowers of plants of the new *Anemone* have reddish purple-colored sepals whereas flowers of plants of the male parent selection have pink-colored sepals.

Plants of the new *Anemone* can also be compared to plants of *Anemone hupehensis* 'Praecox', not patented. In side-by-side comparisons, plants of the new *Anemone* and 'Praecox' differ primarily in plant habit as plants of the new *Anemone* are shorter and more compact than plants of 'Praecox'.

Plants of the new *Anemone* can also be compared to plants of *Anemone* x *hybrida* 'Red Riding Hood', not patented. In side-by-side comparisons, plants of the new *Anemone* and 'Red Riding Hood' differ primarily in growth habit as plants of the new *Anemone* are vigorous than plants of 'Red Riding Hood'.

BRIEF DESCRIPTION OF THE PHOTOGRAPHS

The accompanying colored photographs illustrate the overall appearance of the new *Anemone* plant showing the colors as true as it is reasonably possible to obtain in colored reproductions of this type. Colors in the photographs may differ slightly from the color values cited in the detailed botanical description which accurately describe the colors of the new *Anemone* plant.

The photograph on the first sheet (FIG. 1) is a side perspective view of a typical plant of 'IFANFA' in a container.

Figure 2:
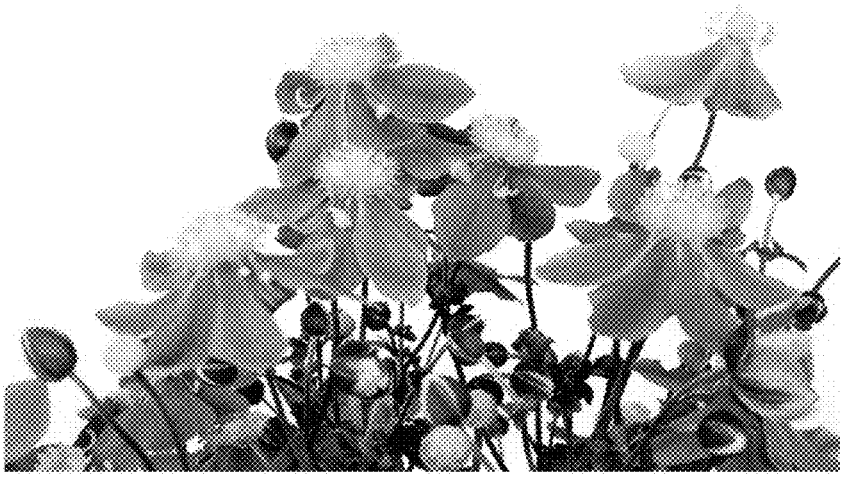

The photograph at the top of the second sheet (FIG. 2) is a close-up view of typical flowers and flower buds of 'IFANFA'.

Figure 3:
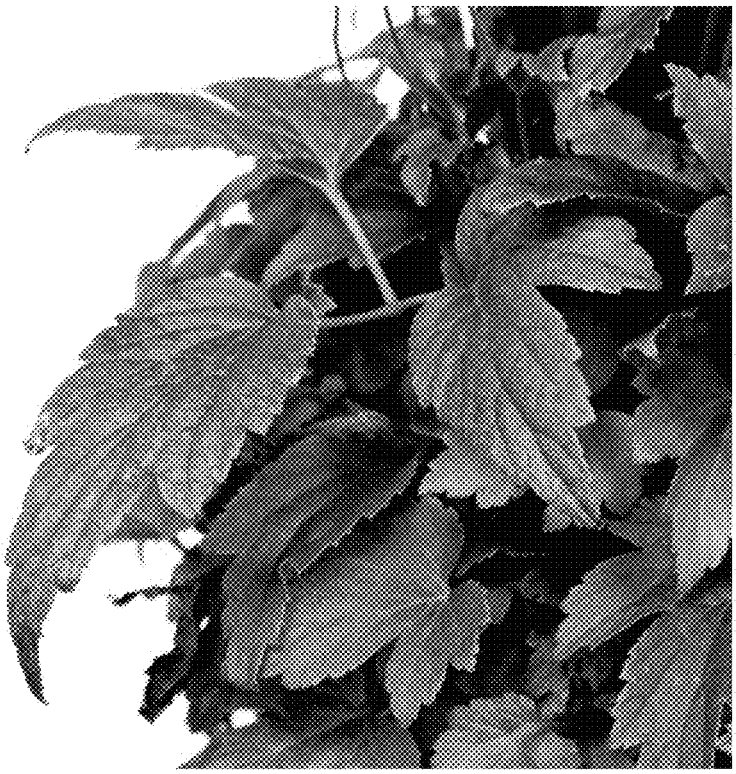

The photograph at the bottom of the second sheet (FIG. 3) is a close-up view of typical leaves of 'IFANFA'.

DETAILED BOTANICAL DESCRIPTION

The aforementioned photographs and following observations, measurements and values describe plants grown during the late summer in 19-cm containers in an outdoor nursery in Heerhugowaard, The Netherlands and under cultural practices typical of commercial *Anemone* production. During the production of the plants, day temperatures ranged from 16° C. to 30° C. and night temperatures ranged from 8° C. to 18° C. Plants were 15 weeks old when the photographs and description were taken. In the following description, color references are made to The Royal Horticultural Society Colour Chart, 2015 Edition, except where general terms of ordinary dictionary significance are used.

Botanical classification: *Anemone hupehensis* 'IFANFA'.

Parentage:

*Female, or seed, parent*.—Proprietary selection of *Anemone hupehensis* identified as code number 148-14-k020-11, not patented.

*Male, or pollen, parent*.—Proprietary selection of *Anemone hupehensis* identified as code number 148-12-k002-01, not patented.

Propagation:

*Type*.—In vitro meristem culture.

*Time to initiate roots, summer*.—About ten days at temperatures about 22° C.

*Time to initiate roots, winter*.—About 15 days at temperatures about 20° C.

*Time to produce a rooted young plant, summer*.—About 42 days at temperatures about 20° C.

*Time to produce a rooted young plant, winter*.—About 50 days at temperatures about 20° C.

*Root description*.—Fine, moderately fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous perennial; upright and uniform plant habit with basal stems and leaves developing in basal rosettes; numerous basal rosettes developing per plant; ovate in overall plant shape; moderately vigorous to vigorous growth habit; moderate growth rate.

*Plant height, soil level to top of foliar plane*.—About 45.8 cm.

*Plant height, soil level to top of floral plane*.—About 53.3 cm.

*Plant diameter*.—About 39 cm.

Branch description:

*Quantity per plant*.—About 26.

*Length*.—About 26.8 cm.

*Diameter*.—About 3 mm.

*Internode length*.—About 13.5 cm.

*Strength*.—Moderately strong.

*Aspect*.—Upright to about 5° from vertical.

*Texture and luster*.—Sparsely to moderately pubescent; moderately glossy.

*Color, developing*.—Close to 144B; surfaces exposed to full sun, close to 144A and slightly tinged with close to N186C.

*Color, developed*.—Close to 144A; surfaces exposed to full sun, slightly tinged with close to N186C.

Leaf description:

*Arrangement, basal leaves*.—Alternate; compound.

*Arrangement, cauline leaves*.—Opposite; simple.

*Length, basal leaves*.—About 13 cm.

*Width, basal leaves*.—About 11.5 cm.

*Length, cauline leaves*.—About 5.7 cm.

*Width, cauline leaves*.—About 4.3 cm.

*Length, basal leaflets*.—Terminal leaflets, about 9.3 cm and lateral leaflets, about 6.2 cm.

*Width, basal leaflets*.—Terminal leaflets, about 4.4 cm and lateral leaflets, about 4.1 cm.

*Length, cauline leaflets*.—Terminal leaflets, about 6 cm and lateral leaflets, about 3.7 cm.

*Width, cauline leaflets*.—Terminal leaflets, about 2 cm and lateral leaflets, about 2.3 cm.

*Shape, basal and cauline leaves*.—Palmately three-lobed to trifoliate; lobed to cleft, depth of sinuses are deep and convergent; in overall outline, broadly ovate; moderately carinate and slightly reflexed.

*Shape, basal leaflets*.—Ovate to elliptic.

*Shape, cauline leaflets*.—Narrowly ovate to narrowly elliptic.

*Apex, basal and cauline leaflets*.—Acute to narrowly acute.

*Base, basal and cauline leaflets*.—Truncate to hastate or obtuse.

*Margin, basal and cauline leaflets*.—Biserrate.

*Texture and luster, basal and cauline leaflets, upper surface*.—Sparsely pubescent; not rugose; slightly glossy.

*Texture and luster, basal and cauline leaflets, lower surface*.—Sparsely pubescent; not rugose; matte.

*Venation pattern, basal and cauline leaflets*.—Laciniate.

*Color, basal and cauline leaflets*.—Developing leaflets, upper surface: Close to between 143A and 144A. Developing leaflets, lower surface: Close to 138B. Fully expanded leaflets, upper surface: Close to NN137A to NN137B; venation, close to 144A. Fully expanded leaflets, lower surface: Close to 148B; venation, close to 146D.

*Leaf petioles*.—Length, basal leaves: About 11.8 cm. Diameter, basal leaves: About 2 mm. Length, cauline leaves: About 1.9 cm. Diameter, cauline leaves: About 2 mm. Strength, basal and cauline leaves: Strong. Texture and luster, basal and cauline leaves, upper and lower surfaces: Moderately pubescent; slightly glossy. Color, basal and cauline leaves, upper and lower surfaces: Close to 144A.

Flower description:

*Flower arrangement and flowering habit*.—Single-type rotate flowers arranged in terminal compound cymes; freely flowering habit with ten flowers per inflorescence and about 260 flowers developing per plant during the flowering season; flowers face mostly upright to slightly outwardly.

*Fragrance*.—None detected.

*Natural flowering season*.—Plants of the new *Anemone* flower during the summer into the autumn in The Netherlands.

*Flower longevity*.—Individual flowers last about ten days on the plant; flowers not persistent.

*Inflorescence height*.—About 23.9 cm.

*Inflorescence diameter*.—About 16.7 cm.

*Flower diameter*.—About 5.7 cm.

*Flower length* (*depth*).—About 2.5 cm.

*Flower buds*.—Length: About 1.3 cm. Diameter: About 1.1 cm. Shape: Broadly ovate. Texture and luster: Moderately pubescent; matte. Color: Close to between N186C and 187A; proximally, tinged with close to 147C.

*Petals*.—Absent.

*Sepals*.—Quantity and arrangement: About seven, or occasionally eight, arranged in two whorls. Length, lower whorl: About 2.5 cm. Length, upper whorl: About 3.7 cm. Width, lower whorl: About 1.6 cm. Width, upper whorl: About 2.1 cm. Shape, lower whorl: Ovate. Shape, upper whorl: Elliptic to obovate; slightly concave. Apex, lower and upper whorls: Obtuse to bluntly acute. Base, lower and upper whorls: Cuneate. Margin, lower and upper whorls: Entire; not undulate to slightly undulate. Texture and luster, upper and lower whorls, upper surface: Smooth, glabrous; not rugose; matte. Texture and luster, upper and lower whorls, lower surface: Densely pubescent; not rugose; slightly glossy. Color: When opening, lower whorl, upper surface: Close to N79C. When opening, upper whorl, upper surface: Close to 72A and N79C. When opening, lower whorl, lower surface: Close to N79C tinged with close to 147C. When opening, upper whorl, lower surface: Close to 71D, N79B and N79C. Fully opened, lower whorl, upper surface: Close to between N79C and N186D; venation, similar to lamina colors; color does not change with subsequent development. Fully opened, upper whorl, upper surface: Close to 71B; towards the center and base, close to N79C; venation, similar to lamina colors; color does not change with subsequent development. Fully opened, lower whorl, lower surface: Close to N79B; venation, similar to lamina color; color does not change with subsequent development. Fully opened, upper whorl, lower surface: Close to 70B and N77B; venation, similar to lamina colors; color does not change with subsequent development.

*Peduncles*.—Length: About 16.8 cm. Diameter: About 2 mm. Aspect: About 20° from lateral branch axis. Strength: Strong. Texture and luster: Moderately to densely pubescent; slightly glossy. Color: Close to 146B to 146C; distally, strongly tinged with close to 200B.

*Pedicels*.—Length: About 8.7 cm. Diameter: About 1.75 mm. Aspect: Upright to about 25° from the peduncle axis. Strength: Moderately strong. Texture and luster: Densely pubescent; slightly glossy. Color: Close to 146B; surfaces exposed to full sun, strongly tinged with close to 187A.

*Reproductive organs*.—Androecium: Stamen number per flower: About 200. Filament length: About 8 mm. Filament color: Close to 155A. Anther shape: Oblong. Anther size: About 1 mm by 2 mm. Anther color: Close to 13A. Amount of pollen: Moderate. Pollen color: Close to 11D. Gynoecium: Pistil number per flower: About 500. Pistil length: About 0.75 mm. Stigma shape: Club-shaped. Stigma size: About 0.2 mm by 0.2 mm. Stigma color: Close to N144A. Style length: About 0.55 mm. Style color: Close to N144D. Ovary color: Close to 145D.

*Seeds and fruits*.—To date, seed and fruit development have not been observed on plants of the new *Anemone*.

Garden performance: Plants of the new *Anemone* have been observed to have good garden performance and to tolerate temperatures ranging from about −30° C. to about 35° C. and to be suitable for USDA Hardiness Zones 4 through 9.

Pathogen & pest resistance: To date, plants of the new *Anemone* have not been observed to be resistant to pathogens and pests common to *Anemone* plants.

It is claimed:

1. A new and distinct *Anemone* plant named 'IFANFA' as illustrated and described.

* * * * *